United States Patent
Trautmann et al.

(10) Patent No.: US 10,126,224 B2
(45) Date of Patent: Nov. 13, 2018

(54) PARTICLE SENSOR AND METHOD FOR MANUFACTURING A PARTICLE SENSOR (71) Applicant: Robert Bosch GmbH, Stuttgart (DE)

(72) Inventors: Achim Trautmann, Leonberg (DE); Friedjof Heuck, Stuttgart (DE)

(73) Assignee: ROBERT BOSCH GMBH, Stuttgart (DE)

(*) Notice: Subject to any disclaimer, the term of this patent is extended or adjusted under 35 U.S.C. 154(b) by 18 days.

(21) Appl. No.: 14/911,314

(22) PCT Filed: Aug. 14, 2013

(86) PCT No.: PCT/EP2013/067036
§ 371 (c)(1),
(2) Date: Feb. 10, 2016

(87) PCT Pub. No.: WO2015/022028
PCT Pub. Date: Feb. 19, 2015

(65) Prior Publication Data
US 2016/0195464 A1 Jul. 7, 2016

(51) Int. Cl.
G01N 15/06 (2006.01)
G01N 27/18 (2006.01)

(52) U.S. Cl.
CPC ..... *G01N 15/0656* (2013.01); *G01N 15/0606* (2013.01); *G01N 27/18* (2013.01)

(58) Field of Classification Search
CPC ..... G01N 15/606; G01N 15/656; G01N 27/18
See application file for complete search history.

(56) References Cited

U.S. PATENT DOCUMENTS 4,935,289 A * 6/1990 Kikuchi .......... G01N 27/12
156/89.19
7,615,189 B2 * 11/2009 Aslam .......... B82Y 30/00
422/50
(Continued)

FOREIGN PATENT DOCUMENTS

DE 102010038758 2/2012
EP 1037038 9/2000
(Continued)

OTHER PUBLICATIONS

Machine translation of JP H11211689.*
International Search Report for PCT/EP/2013/067036, dated Sep. 19, 2014.

*Primary Examiner* — David Bolduc
(74) *Attorney, Agent, or Firm* — Norton Rose Fulbright US LLP; Gerard Messina (57) ABSTRACT A particle sensor for detecting electrically conductive particles. The particle sensor includes a first electrode structure with at least one electrode and a second electrode structure with at least one electrode. The first electrode structure and the second electrode structure are situated on an electrically insulating base body. An electric potential difference is generatable between an electrode of the first electrode structure and an electrode of the second electrode structure. The base body includes a heating structure for heating the first electrode structure and the second electrode structure, the heating structure being at least partially enclosed by the base body. This makes it possible to protect the heating structure and also to reduce the voltage needed to burn off particles accumulated on the electrode structures. A method for manufacturing a particle sensor is also described.

20 Claims, 4 Drawing Sheets

(56) References Cited

U.S. PATENT DOCUMENTS

| | | | |
|---|---|---|---|
| 7,968,055 B2* | 6/2011 | Brothier | G01N 5/02 422/83 |
| 2005/0225308 A1* | 10/2005 | Orvek | G01N 15/0656 324/71.4 |
| 2006/0016687 A1* | 1/2006 | Wallace | G01N 27/4071 204/515 |
| 2006/0154401 A1* | 7/2006 | Gardner | G01N 27/128 438/53 |
| 2007/0158191 A1* | 7/2007 | Berger | G01N 15/0656 204/421 |
| 2008/0087101 A1* | 4/2008 | Konstandopoulos | F01N 3/022 73/861.42 |
| 2008/0264146 A1* | 10/2008 | Roesch | G01N 15/0656 73/23.33 |
| 2009/0056416 A1* | 3/2009 | Nair | G01N 15/0656 73/28.01 |
| 2009/0126458 A1* | 5/2009 | Fleischer | G01N 15/0656 73/28.01 |
| 2009/0126460 A1* | 5/2009 | Gardner | G01N 33/0031 73/31.06 |
| 2009/0211336 A1* | 8/2009 | Combes | G01N 30/08 73/23.37 |
| 2009/0309571 A1* | 12/2009 | Katsuyama | G01N 15/0656 324/71.1 |
| 2010/0000863 A1* | 1/2010 | Kondo | G01N 15/0656 204/406 |
| 2010/0044246 A1* | 2/2010 | Hall | G01N 15/0656 205/775 |
| 2010/0229629 A1* | 9/2010 | Egami | G01N 15/0656 73/28.01 |
| 2011/0107817 A1* | 5/2011 | Krauss | G01N 15/0656 73/25.03 |
| 2011/0156727 A1* | 6/2011 | Achhammer | F02D 41/1466 324/691 |
| 2011/0252866 A1* | 10/2011 | Tokuda | G01N 15/0656 73/23.31 |
| 2011/0268148 A1* | 11/2011 | King | G01K 17/006 374/31 |
| 2012/0103058 A1* | 5/2012 | Maeda | G01N 15/0656 73/23.33 |
| 2012/0247181 A1 | 10/2012 | Nishijima | |
| 2013/0236907 A1* | 9/2013 | Petersen | B01L 7/52 435/7.1 |

FOREIGN PATENT DOCUMENTS

| | | |
|---|---|---|
| EP | 2228646 | 9/2010 |
| JP | H07244013 A | 9/1995 |
| JP | H0885201 A | 4/1996 |
| JP | H11211689 A | 8/1999 |
| JP | 2000275078 A | 10/2000 |
| JP | 2004144627 A | 5/2004 |
| JP | 2004181964 A | 7/2004 |
| JP | 2004257870 A | 9/2004 |
| JP | 2010067797 A | 3/2010 |
| JP | 2011080926 A | 4/2011 |
| JP | 2011226859 A | 11/2011 |
| JP | 2012093289 A | 5/2012 |
| JP | 2012127907 A | 7/2012 |
| JP | 2013011605 A | 1/2013 |
| WO | WO 2004/097392 | 11/2004 |

* cited by examiner

PARTICLE SENSOR AND METHOD FOR MANUFACTURING A PARTICLE SENSOR

FIELD

The present invention relates to a particle sensor which includes a heatable base body. Moreover, the present invention relates to a method for manufacturing a particle sensor which includes a heatable base body.

BACKGROUND INFORMATION

In many countries, current regulations require sensors for measuring the soot particle concentration in the exhaust gas for vehicles operated with gasoline or diesel fuel. The detection principle of conventional sensors for measuring the soot particle concentration may be based on an accumulation of conductive soot particles on an electrode structure. This accumulation of the electrically conductive particles may be reflected by a drop in the electrical resistance over time, or by an increasing current flow between the electrodes in question. A measuring cycle may start with an unloaded or free sensor, which in the exhaust gas is exposed to the conductive particles. A time period during which the electrical resistance drops below a certain threshold value may be used as a measure for the soot particle concentration in the exhaust gas. To be able to reuse the sensor after a continued accumulation of electrically conductive particles, the sensor may be heated to burn off the accumulated soot, after which another measuring cycle may begin.

For example, the sensor may be heated to the required burnoff temperature by using high voltages and currents in an ohmic heating element. In particular, providing the high voltage requires a high level of electrical engineering effort. In this regard, it is important to note that thick sensors require particularly high voltages, but thin sensors have only limited mechanical stability.

SUMMARY

The present invention relates to a particle sensor for detecting electrically conductive particles, including a first electrode structure with at least one electrode and a second electrode structure with at least one electrode, the first electrode structure and the second electrode structure being situated on an electrically insulating base body, an electric potential difference being generatable between an electrode of the first electrode structure and an electrode of the second electrode structure, and the base body including a heating structure for heating the first electrode structure and the second electrode structure, the heating structure being at least partially enclosed by the base body.

This type of particle sensor is in particular a resistive particle sensor, and may be based on the property that the particles to be detected, which in particular may be formed generally from carbon as soot particles, in particular are electrically conductive. Use is made of the electrical conductivity in order to detect the accumulated soot particles. For this purpose, the particle sensor includes a first electrode structure and a second electrode structure, the first electrode structure and the second electrode structure each including at least one electrode. The electrode structures or the electrodes of the electrode structures are situated on an electrically insulating base body. An electrically insulating base body may in particular be one which is made of an electrically insulating material, or which in principle may be electrically conductive but includes an electrically insulating cover layer. Within the scope of the present invention, "electrically insulating" may be understood in particular to mean that the specific electrical resistance is in a range of ≥1 kohm cm, whereas "electrically conductive" may be understood in particular to mean that the specific electrical resistance is in a range of <1 kohm cm.

In addition, within the scope of the present invention, "thermally insulating" may be understood in particular to mean that the thermal conductivity or heat conductivity is in a range of ≤15 W/m/K, whereas "thermally conductive" may be understood in particular to mean that the thermal conductivity is in a range of >15 W/m/K.

If the electrode structures situated on the base body are now exposed to a gas flow containing the particles to be detected, the particles accumulate on the electrode structures. As a result, current measurements, voltage measurements, capacitance measurements, and/or resistance measurements may be carried out when an electrical potential is built up between the first electrode structure and the second electrode structure, for example due to providing and connecting a suitable voltage source. Conclusions concerning the accumulated particles, and thus the particle concentration, in the gas flow may be drawn in particular based on a change in the flowing current, the prevailing voltage, or the prevailing resistance.

This measuring method may thus be based on the fact that accumulated electrically conductive particles allow a current flow between the electrodes of different electrode structures, or reduce the resistance prevailing between the electrodes. Thus, by quantifying the increase in the current flow or the decrease in the electrical resistance, a conclusion may be drawn, for example, concerning the particles which have accumulated on the electrode structure. This may be possible in particular by an observation of the change in the current flow or in the resistance over time.

After a certain measuring period, accumulated particles may be removed again from the sensor or from the electrode structure in order to regenerate the sensor and start another measuring cycle. This type of particle sensor includes a heating structure for this purpose. The heating structure is used in particular for heating the first and the second electrode structures in such a way that they may be brought to a burnoff temperature which is sufficient to burn off or oxidize the accumulated particles, in particular soot particles, and thus remove them from the electrode structure. Suitable burnoff temperatures may be in a range of 500° C. or higher. In this regard, the heating structure may be made in particular of an electrically and thermally conductive material and used as an ohmic heater.

The heating structure may be at least partially enclosed by the base body. In other words, the heating structure is situated in the base body and is at least partially surrounded by the base body or the base body material. Due to such an integration of the heating structure into the base body, which in particular is made of an electrically and in particular thermally insulating material, the heating structure may on the one hand be electrically insulated, and on the other hand, chemically passivated. The heating structure is thus stable against external corrosive attacks or other influences. The heating structure is particularly mechanically stable or stabilized, and is thermally insulated with respect to a mechanical connection of the active measuring area, as the result of which, flow of the generated heat into a housing, for example, due to heat conduction, may be minimized or prevented.

In addition, this type of particle sensor is manufacturable in a particularly simple and cost-effective manner, since only few, and in particular cost-effective, process steps are required.

In particular, however, not only is the heating structure thermally insulated with respect to an anchoring or mechanical connection, but also the generated heat may be well localized. In other words, the generated heat may be focused generally on the surroundings of the heating structure; i.e., for the burnoff, the heat output may be concentrated generally on the active sensor surface or the electrode structures, since a thermal decoupling from the surroundings and in particular from the coupling to a housing is achieved. Particularly effective heating of the electrode structures for removal of accumulated electrically conductive particles may thus be made possible. It is thus possible for accumulated particles to be removed using only low voltages or currents. The requirements regarding current and/or voltage for regenerating the particle sensor may thus be kept particularly low, which may result in a great cost advantage in the manufacture of a particle sensor.

Heating of the electrode structures may be easily possible despite the heating structure being situated in a base body which is also thermally insulating, and which may have a thermal conductivity in a range of 1 W/mK, for example, since a gradient of the heat distribution usually occurs over the comparatively large length or width with respect to the height, i.e., the surface extension of the base body material, but along the height, also due to the small distance between the heater layer and the electrode structures, which in particular may be in a range of 1 µm, sufficient heat for generating the suitable burnoff temperature may pass from the heating structure to the electrode structures.

A burnoff of the particles accumulated on the electrode structures may thus be easily achieved due to this type of heatable base body for a particle sensor, also referred to as a diaphragm, even with comparatively large electrically insulating layers or substrates, for example 5 mm×5 mm. Very thin particle sensors and thin base bodies may thus be provided which have sufficient mechanical stability and which require little current or voltage for regenerating the electrodes. In addition, a customized thermal as well as electrical connection of the electrode structures, for example, and of the heating structure, for example to the electronic system of a vehicle, may be possible. Due to focusing the heat onto the area of the electrode structures, a burnoff using 12 V, for example, which is common in a vehicle, may be carried out.

This type of particle sensor thus includes a mechanically stable heating structure, in a base body, which is thermally insulated and electrically resistive with respect to an anchoring or connection. The integration of the electrically resistive heater and the manufacture of the base body or the diaphragm may take place in the same process steps. This allows the fabrication of an active, stable base body for a soot particle sensor, based on comparatively simple and cost-effective process steps.

The processes necessary for this purpose are basically well known in particular from the field of micromechanics.

Within the scope of one embodiment, the base body may be made of silicon dioxide, and/or the heating structure may be made of silicon. Such materials may be processed in a particularly easy manner using conventional methods in micromechanics, so that a particularly simple, technically mature, and cost-effective manufacturing method is possible. In addition, silicon dioxide, for example, has a heat conductivity that is approximately 100 times poorer than silicon, and also has a good electrical insulation capacity, for which reason it is particularly suited as both a thermal and an electrical insulator. In addition, a particularly simple manufacturing method may be made possible in this embodiment, in which the base body may be manufacturable, at least partially, based on thermal oxidation processes in particular. One advantage in particular may be seen in that an electrically and thermally conductive base layer may be chemically converted, at least partially, into an electrically and thermally insulating material which encloses the electrically resistive heater.

Within the scope of another embodiment, the heating structure may be completely enclosed by the base body. In this embodiment, heat losses due to thermal conduction may be reduced in a particularly reliable manner. The requirements for the current flowing during a regeneration or for the voltage applied for this purpose may thus be kept particularly low. This results in particularly cost-effective operation and installation of this type of sensor. In addition, protection of the heating structure against corrosive attacks, for example, may be possible in a particularly effective manner. A complete enclosure of the heating structure by the base body may mean in particular a shell-like enclosure. Within the meaning of the present invention, this may also mean that the areas of the heating structure which are hot or which are to be heated, which are intended to act on the electrode structures and are situated adjacently to same, are completely embedded in the base body or are enclosed by same; however, such connections, for example, do not have to be enclosed by the base body, or may be situated outside the base body.

Within the scope of another embodiment, the heating structure may have a net-like conductor structure situated in the base body. Due to an in particular two-dimensional net-like conductor structure, the area to be heated may be adapted to the area of application in a particularly advantageous manner. In particular, the net-like conductor structure, which in particular may be made of silicon, may have a size and/or assume a position corresponding to the electrode structure(s). The conductor structure may generate a heating effect in particular due to Joule heat or an ohmic resistance, which makes possible a burnoff or a regeneration of the electrode structures, in a conventional manner, by applying a voltage or due to flowing current. In addition, a large area may be uniformly heated due to a net-like structure, so that generally no temperature gradient or only a small temperature gradient results over the length or over the width of the area to be heated. Another advantage of a net-like conductor structure may be considered in that the corresponding conducting tracks are well linked with or connected to one another. This results in the advantage that, even when individual conducting tracks are interrupted, for example due to damage to the sensor, further heating may be easily possible. A net structure or a net-like structure may be understood in particular to mean a structure which includes an arrangement of a plurality of conducting tracks which are connected to or linked with one another, in particular multiple times.

Within the scope of another embodiment, the heating structure, in particular the net-like conductor structure, may include conducting tracks which have, at least in part, a width in a range of ≤500 nm. These types of conducting tracks, which in particular may be an integral part of the net-like structure, may generate a good heating effect, even at low currents. For this reason, operation and electrical control of a particle sensor in this embodiment is possible in a particularly cost-effective manner. The conducting tracks do not have to have such a width or such a cross section at every location, but, rather, may also be shaped with a cross section or width which varies along its course, so that they need to have such a width only in a partial area.

Another advantage of these types of conducting tracks, made in particular of silicon, may lie in the temperature-dependent electrical resistance behavior. For doped semiconductors, for example, the electrical resistance has a maximum with regard to temperature. At this maximum, the extrinsic conductivity becomes an intrinsic conductivity. This maximum and the subsequent drop in the electrical conductivity increase the control effort for setting a defined temperature profile. The position of the maximum may be shifted to higher temperatures, for example due to a high level of doping, or also due to a very small conductor cross section, such as in particular in a range of ≤500 nm in particular, in a range of 100 nm in particular, for example due to a so-called "minority charge carrier exclusion effect."

Within the scope of another embodiment, a homogenization area for homogenizing the temperature of the base body may be provided which is surrounded by the heating structure, in particular it being possible for the homogenization area to be made of electrically and/or thermally conductive material. Particularly advantageous homogenization of the temperature may be created in this embodiment, as the result of which the electrode structures may be heatable in a particularly uniform manner. In addition, temperature peaks may be avoided, as the result of which damage may be avoided and the required electrical power used may be minimized. In particular, the homogenization area may be a planar area in which a temperature plateau having temperatures of up to +200° C. maximum above the burnoff temperature may occur; in particular, temperatures in a range of higher than 1000° C. may be avoided. For this purpose, the homogenization area may have a suitable planar extension, and in particular may have a settable electrically and/or thermally conductive material portion.

Within the scope of another embodiment, the homogenization area may be surrounded by an electrically insulating area which is enclosed by the heating structure. In this embodiment, a temperature homogenization may be achieved in particular by an increased thermal dissipation having a settable design, or by a setting of the electrical resistance which uses the introduced electrical heat output locally in a targeted manner.

Within the scope of another embodiment, the base body and the heating structure are situated in a first layer and the electrode structures are situated in a second layer, the second layer being situated on the first layer. In this embodiment, a sensor of this type thus includes layers, which in particular may be directly adjacent. In this way, the layer of the electrode structure may be heated by the heating structure particularly advantageously and without heat losses. In addition, in this embodiment a particularly compact design of the particle sensor is possible. A high level of variability of the use of this type of particle sensor is thus provided.

With regard to further advantages and technical features of the particle sensor according to the present invention, explicit reference is hereby made to the explanations in conjunction with the method according to the present invention, the figures, and the description of the figures.

A further subject matter of the present invention relates to a method for manufacturing a particle sensor, in particular a particle sensor according to the present invention, including the following method steps:

a) providing a base body which includes a base layer, an electrically insulating layer situated on the base layer, and an electrically conductive layer situated on the electrically insulating layer;

b) introducing at least one recess into the electrically conductive layer for structuring the electrically conductive layer;

c) applying an electrically insulating cover layer to the electrically conductive layer; and d) applying at least two electrode structures to the cover layer.

Such a method is thus used in particular for manufacturing a particle sensor as described above.

In first method step a), initially a base body is thus provided which includes a base layer, an electrically insulating layer situated on the base layer, and an electrically conductive layer situated on the electrically insulating layer. The base layer may be used in particular for stability of the base body, in particular during the manufacturing method, and may have a large thickness. The appropriate thickness may be selected as a function of the required stability or the thickness of the electrically insulating layer and/or of the electrically conductive layer. The thicknesses may be in a range of approximately 700 μm, for example. The base layer may be electrically and/or thermally insulating, or also preferably electrically and/or thermally conductive. The electrically insulating layer may have a thickness in a range of 1 μm, for example. In addition, the electrically conductive layer situated on the electrically insulating layer may have a thickness in a range of ≥5 μm to ≤100 μm. Furthermore, from a manufacturing standpoint, for example, it may be advantageous for the electrically conductive layer and the base layer to be made of the same material.

Starting from the base body, at least one, in particular a plurality of, recesses is introduced into the electrically conductive layer in further method step b). The recess or the recesses may extend in particular to a depth which adjoins the electrically insulating layer, so that the electrically insulating layer is exposed but its thickness is not, or is not significantly, changed. Such a termination of the shape of the recess at a defined depth for the structuring of the electrically conductive layer may be achieved when a sufficiently great difference of the chemical or physical properties between the two layers is selected, for example between silicon and silicon dioxide, and in particular with regard to the method to be selected for forming the recesses. One example of a suitable method for this type of structuring or for introducing recesses is a photolithographic method for defining the recesses, and a subsequent deep reactive ion etching method for structuring the recesses into the electrically conductive layer. This may take place within the scope of microstructuring. For example, within the scope of a deep reactive ion etching method, the forming of the recesses in the electrically conductive layer, containing silicon, for example, may advantageously be stopped in a well-defined manner due to chemical differences from the electrically insulating layer. By introducing the recesses into the electrically conductive layer, which in particular is situated opposite from the base layer, for example a net-like and in particular a two-dimensional net-like structure may be provided. In principle, method step b) may be used for structuring the base body and also for forming in particular a plurality of functional areas.

When a cover layer, and in particular an electrically insulating layer as cover layer, is applied to the electrically conductive layer in further method step c), the created recesses may be filled with the electrically insulating material of the cover layer, as the result of which an essentially flat contour surface in the area of the cover layer is creatable.

The electrically conductive layer which is embedded in the electrically and thermally insulating cover layer may subsequently be used as a heating structure. Due to applying the electrically and thermally insulating cover layer, the heating structure may be insulated in such a way that the heat generated by the heating structure may be well localized, for example in a subsequent use on the electrode structures. The electrically insulating cover layer together with the further electrically insulating layer may form the base body, which at least partially encases the heating structure.

The electrode structures may be applied on the cover layer in further method step d). It may be advantageous for the electrode structures to be applied in the area in which the heating structure is situated, in order to be able to focus the generated heat onto the electrode structures. When a sensor manufactured in this way is used, the electrode structures may be used as a measuring area for detecting electrically conductive particles, and after a measuring cycle may be regenerated by the heating structures. An application of the electrode structures may take place by physical and/or chemical deposition, for example by vaporization or sputtering, of high-melting chemically inert materials, for example platinum, tungsten, or silicon carbide.

Due to the method described above, it is possible to integrate a heating structure into a base body layer, with only a few process steps being necessary. This may be achievable by using conventional and technically mature methods in particular in the field of microtechnology. In addition, by a suitable selection of the base body, the heating structure may be integrated into the base body, so that a final deposition and structuring of the heating structure is dispensed with.

Within the scope of one embodiment, a chemically convertible layer may be used as the electrically conductive layer, and the electrically insulating cover layer may be created by a chemical conversion of the electrically conductive layer. For example, a chemical conversion may include an oxidation or formation of an oxide layer, or the chemical conversion may include nitriding, i.e., forming a nitride layer. In addition, the electrically insulating layer may also be simply deposited, such as by a chemical gas phase deposition, for example. Within the meaning of the present invention, an oxide layer may be created in particular by exposing the electrically conductive chemically convertible or oxidizable layer, which is present anyway, to an oxidizing environment, for example at high temperatures, for example $\geq 800$ to $\geq 1200°$ C., with simultaneous addition of oxygen or steam. The cover layer may thus be applied in a particularly simple manner, namely, by an easily carried out oxidation of the electrically conductive material. It may be advantageous in particular for the introduced recesses to be closed by the oxidation. This is because the oxide may on the one hand grow inwardly into the oxidizable material, and on the other hand may grow outwardly. In addition, the oxidation ends automatically when all depressions in the electrically conductive layer are closed by the oxide layer, which may involve process-related advantages, or as soon as the process is terminated. The cover layer may thus be applied particularly easily to the structures which are created in the method by introducing the recesses, and it is not necessary to use masks or the like. This is because the site of the oxidation or the position of applying the cover layer may be exactly determined in advance via the configuration of the structure in method step b). The same applies for nitriding of the electrically conductive layer. Suitable reaction conditions for nitriding, such as for forming a silicon nitride layer, may include a temperature in a range of $\leq 500°$ C. to $\leq 1000°$ C., with addition of silane and ammonia.

In this regard, it is to be mentioned that via a suitable chemical conversion of the electrically conductive layer into an electrically insulating layer, whereby the material of the electrically conductive layer is consumed during the conversion, structures having dimensions of $\geq 1$ μm may be converted into electrically conductive structures of 100 nm. Since the height of the structure compared to the width is decreased only slightly during the conversion, it is thus possible to create structures having extremely high aspect ratios of 1:200 (width to height).

Due to the method described above, in this embodiment it may be possible in a particularly advantageous manner to also apply electrically and in particular thermally insulating layers, which are present in particular in a thickness of $\geq 20$ μm, by a chemical conversion. This is an advantage over conventional methods, since, due to a conventional oxidation, for example, layer thicknesses of up to 3 μm which are achievable in a technically practical manner are possible here, or greater layer thicknesses of up to 10 μm, in particular due to deposition, such as chemical deposition, would be possible.

Within the scope of another embodiment, the base layer and/or the electrically conductive layer may be made of silicon, and/or the electrically insulating layer may be made of silicon dioxide.

In this embodiment, the base body may thus be a so-called "silicon on insulator" (SOI) base body, or also an epitaxially grown silicon, or, as a very cost-effective variant, a polycrystalline silicon layer on an oxidized base body. The layers made of silicon may be highly doped independently of one another, for example with phosphorus, boron, or arsenic, and may thus have a particularly good electrical conductivity. In addition, they are separated from one another by a relatively thin layer of an electrically insulating material, in particular made of silicon dioxide. In this embodiment, known and easily obtainable base bodies which are particularly cost-effective may thus be used, which may make the manufacturing method particularly easy and cost-effective.

Within the scope of another embodiment, the at least one recess may be designed as a circular opening which in particular is closed at the circumference. Circular openings may be created particularly easily. In addition, due to forming circular openings, a net-like conductor structure which is particularly suitable for a heating structure of a particle sensor may be created particularly easily. The net-like conductor structure may then be formed by at least a portion of the material which is still present next to the openings and which has not been removed during the structuring in method step b). In particular, a plurality of circular openings may be provided within the meaning of the present invention, whereby it is not ruled out within the scope of the present invention that openings which are not completely closed at the circumference may also be provided. In addition, the openings may have a diameter in a range of $\geq 2$ μm to $\leq 3$ μm, for example.

Within the scope of another embodiment, a plurality of recesses, in particular circular openings, which are in a hexagonal arrangement may be created. In particular, for a hexagonal arrangement of openings or in particular of circular openings, or an arrangement of the openings in a hexagonal structure, an isotropic structure may be created. Such an isotropy of this structure provides in particular increased stability of the structure, such as against anisotropic stresses, since there is no clear preferred direction. In addition, the isotropy also allows homogeneous oxide growth, since it does not require an alignment with the crystallographic directions.

In addition, complete oxidation may be dispensed with for integrating a heater into the layer of the base body. A hexagonal arrangement may mean in particular an arrangement according to a top view onto a hexagonal crystal structure.

With regard to further advantages and technical features of the method according to the present invention, explicit reference is hereby made to the explanations in conjunction with the particle sensor according to the present invention, the figures, and the description of the figures.

BRIEF DESCRIPTION OF THE DRAWINGS

Further advantages and advantageous embodiments of the subject matters according to the present invention are shown in the figures and explained below. It is pointed out that the figures are only descriptive in nature, and are not intended to limit the present invention in any way.

DETAILED DESCRIPTION OF EXAMPLE EMBODIMENTS

Figure 1:
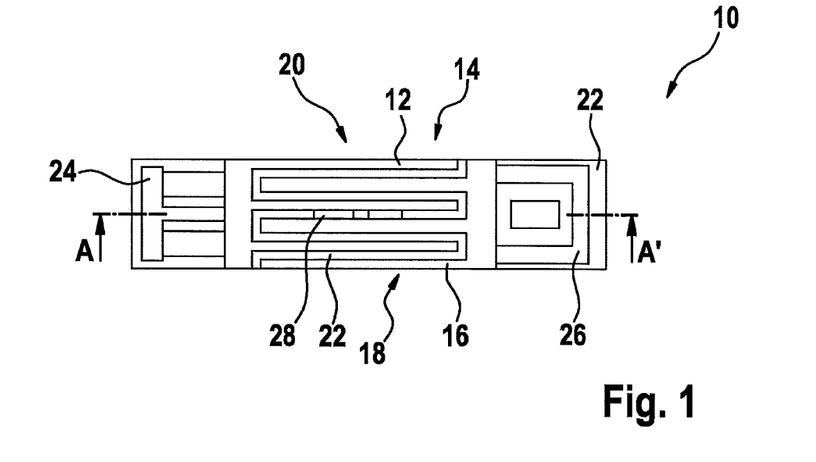
FIG. 1 shows a schematic top view onto one specific embodiment of a particle sensor according to the present invention.

FIG. 1 shows a particle sensor 10 according to the present invention. This type of particle sensor 10 may be situated, for example, in the exhaust system of a motor vehicle. Such a particle sensor 10 may determine, for example, the functioning of a particle filter situated in the exhaust system of a motor vehicle, or may determine the particle emissions.

A particle sensor 10 of this type is thus used in particular for detecting electrically conductive particles. Particle sensor 10 may in particular include a first electrode structure 14 with at least one electrode 12, and a second electrode structure 18 with at least one electrode 16. First electrode structure 14 and second electrode structure 18 form an electrode system 20. Electrode system 20 or electrode structures 14, 18 may form a system made up of interdigital electrodes which mesh together in a comb-like manner, as shown in FIG. 1. First electrode structure 14 and second electrode structure 18 are situated on an electrically insulating base body 22. An electric potential difference may be generatable between an electrode 12 of first electrode structure 14 and an electrode 16 of second electrode structure 18.

For this purpose, a voltage source (not shown), for example, may be connected to electrodes 12, 16. In order to detect the particles, such as soot particles in particular, contained in a gas flow, the current flow generated by the potential difference, or the resistance or the capacitance between the different electrode structures 14, 18, may be ascertained. For this purpose, electrode structures 14, 18 are electrically connected to an electrical terminal or to an electrical dissipation line 24, 26.

In order to remove the accumulated particles from electrode structures 14, 18 after a certain measuring cycle or after a certain measuring period, particle sensor 10 includes a heating structure 28. Heating structure 28 may be used in particular for heating first electrode structure 14 or second electrode structure 18 to a burnoff temperature at which the accumulated particles are oxidized and may thus be removed from electrode structures 14, 18. It is thus apparent to those skilled in the art that heating structure 28 may be adapted in particular to the size, position, or extension of electrode structures 14, 18, and may thus be provided in an extension which is greater than or equal to the extension of electrode system 20, so that entire electrode system 20 may advantageously be subjected to a regeneration. Heating structure 28 may optionally be locally replaced by a homogenization area 56, as explained in greater detail below.

Heating structure 28 may be enclosed in particular by base body 22 at least partially, in particular completely, in a shell-like manner, for example. This is illustrated in particular in FIG. 2, which shows a sectional view along segment A-A' from FIG. 1.

Figure 2:
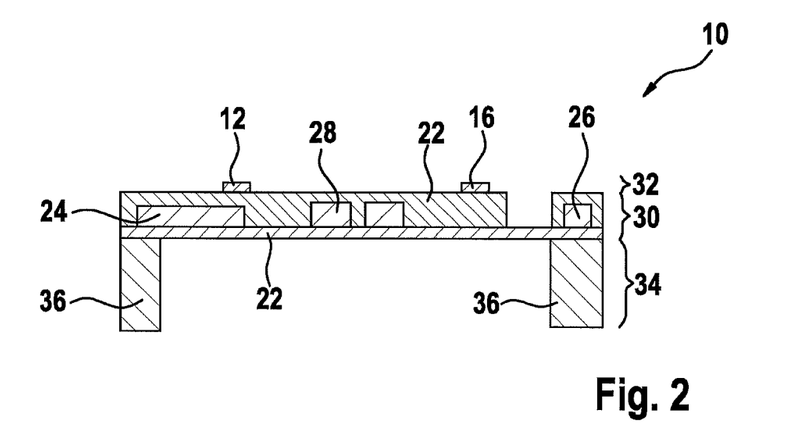
FIG. 2 shows a schematic sectional view along segment A-A' from FIG. 1.

In FIG. 2 it is apparent that heating structure 28 is situated within base body 22, i.e., is completely surrounded by the material of base body 22.

Base body 22 may be made of silicon dioxide, for example, whereas heating structure 28 may be made of silicon, for example. Alternative materials for base body 22 include silicon nitride, aluminum oxide, or titanium oxide, for example, whereas alternative materials for heating structure 28 may include metals in particular having a melting point of >1000° C., for example titanium. In addition, electrode system 20 or electrode structures 14, 18 may be made of platinum, tungsten, and silicon carbide.

It is also apparent in FIG. 2 that base body 22 and heating structure 28 are situated in a first layer 30, and electrode structures 14, 18 are situated in a second layer 32. Second layer 32 may be situated on first layer 30. In addition, in particular mechanical connections 36 for fastening and electrically contacting particle sensor 10 may be situated in a third layer 34 situated below first layer 30.

A method for manufacturing this type of particle sensor 10 is shown in FIGS. 3 through 6.

Figure 3A:
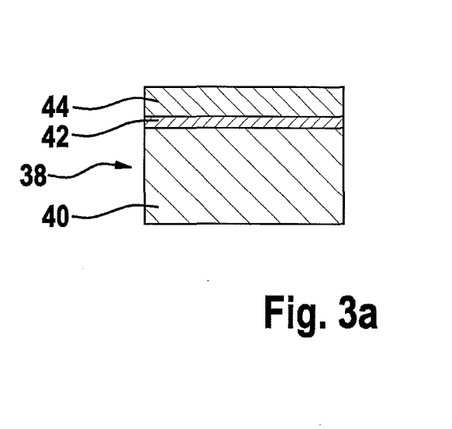
FIG. 3a shows a method step for manufacturing a particle sensor, in a cross-sectional view.
Figure 3B:
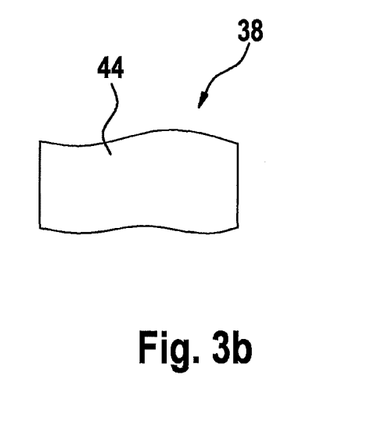
FIG. 3b shows the method step from FIG. 3a in a top view.

A base body 38 which includes a base layer 40, an electrically insulating layer 42 situated on base layer 40, and an electrically conductive layer 44 situated on electrically insulating layer 42 is provided in a method step a) according to FIG. 3. FIG. 3a shows a cross section of base body 38, whereas FIG. 3b shows a top view onto base body 38 or onto electrically conductive layer 44. Electrically conductive layer 44, the same as base layer 40, may be made of silicon. The silicon may be highly doped, for example. For example, the silicon may contain doping materials such as phosphorus, boron, and arsenic, whereby the doping strength may extend to the saturation limit of the silicon. Particularly good electrical conductivity may be achievable in this way. Alternative materials for the base layer include quartz, steel, and titanium, for example. Electrically insulating layer 42 may in particular be made of silicon dioxide.

If base layer 40 is made of the same material as top electrically conductive layer 44, this has process-related advantages due to the uniform process control, since essentially the same handling steps may be used.

Figure 4A:
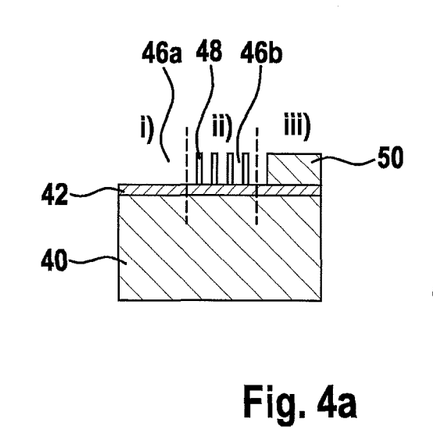
FIG. 4a shows a further method step for manufacturing a particle sensor, in a cross-sectional view.
Figure 4B:
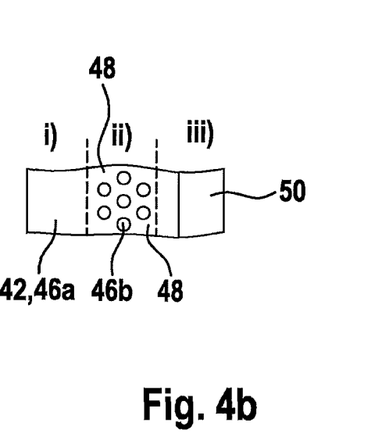
FIG. 4b shows the method step from FIG. 4a in a top view.

The surface of base body 38 or in particular top electrically conductive layer 44 may be structured in a further method step b) according to FIG. 4. For this purpose, for example a photolithographic process and a subsequent deep etching process may be used. In particular, at least one, in particular a plurality of, recesses 46 may be introduced into electrically conductive layer 44 in method step b). Electrically conductive layer 44 may be divided generally into three, for example, different functional areas.

Electrically conductive layer 44 may be removed, generally completely and unstructured, in a first functional area i). This may be possible by providing a recess 46a having very large dimensions. A reduction of the thermal coupling to base body 22 may thus be made possible by completely removing the electrically conductive material of electrically conductive layer 44, in particular the silicon, in area i). In addition, no electrical heating takes place in this area. This structuring thus allows the electrical heat output to be diverted to other areas in a targeted manner. However, this should take place in conjunction with a reduction in the mechanical stability of the layer of the electrically insulating material, in particular a silicon dioxide diaphragm. In other words, it should be ensured that particle sensor 10 has sufficient stability.

In addition, structured recesses 46b, between which protrusions 48 remain, may be introduced into a further functional area ii). Protrusions 48 may be used for a subsequent function of particle sensor 10 as a heating structure 28, and in particular are designed as a net-like structure. In particular, as shown in FIG. 4b, in area ii), recesses 46b are designed as circular, at least partially closed, openings arranged in relation to each other in a hexagonal shape. However, the openings may also have other shapes, such as circular openings arranged in particular in a hexagon. The openings may thus in particular have a honeycomb structure or a honeycomb hole structure. Squares, lines, rectangles, or also spiral-shaped structures would also be possible; this listing is not to be construed to be exhaustive. Thus, in area ii) the creation of a relatively thick layer of an electrically insulating material, such as in particular a silicon dioxide layer, with a heating structure 28 incorporated therein or buried in same, may take place in one or two process steps. This allows a significant process-related advantage.

A further functional area iii) generally includes an area 50 of untreated material of electrically conductive layer 44, and may be used in a function of particle sensor 10, for example, as an electrical connection 24, 26 or attachment of heating structure 28 and/or of electrode system 20. On the other hand, area 50 of electrically conductive layer 44 may be used for a particularly homogeneous temperature distribution on or in base body 22. The surface is oxidized in area iii), but since the structuring is absent, the electrically conductive layer remains having a sufficient unstructured thickness. This area may thus remain as an in particular highly thermally and electrically conductive area, such as a silicon area in particular. The remaining silicon is hereby separated, electrically and in terms of the process, from base layer 40 or the bulk area by electrically insulating layer 42. Cover layer 52, which results from a chemical conversion, may also be strengthened by additionally depositing a further insulating layer, which may result in planarization of cover layer 52.

The possibility, in principle, of implementing a plurality of, such as three in particular, different functional areas i), ii), iii) in one process flow as described above represents a significant difference from a full-surface deposition of the electrically insulating layer, such as silicon dioxide in particular. Rather, specific properties may be assigned to the individual functional areas in a particularly simple manner and by using methods that are easy to use, as described with regard to the individual areas; the arrangement of the functional areas is not limited to the arrangement shown. This is possible in a particularly advantageous manner in conjunction with the oxidative creation of an electrically insulating layer, in particular as a base body material, as explained below with regard to method step c). In particular, thick silicon dioxide layers ≥1 μm may be set very precisely, and thus, an exact process control for the remaining silicon structures may be set.

Figure 5A:
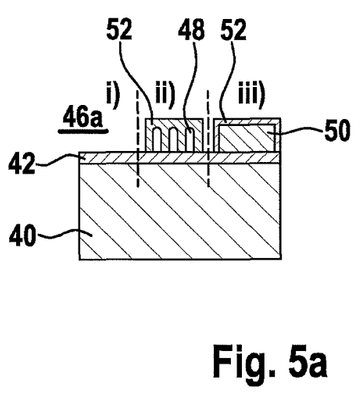
FIG. 5a shows a further method step for manufacturing a particle sensor, in a cross-sectional view.
Figure 5B:
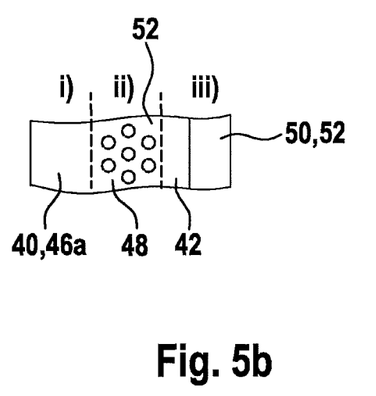
FIG. 5b shows the method step from FIG. 5a in a top view.

In further method step c), as shown in FIGS. 5a and 5b, an electrically insulating cover layer 52 may also be applied to electrically conductive layer 44 or on the structures resulting from conductive layer 44, for example protrusions 48 or 50, which are indicated in a purely schematic manner but which, understandably, are situated below layer 52. Electrically insulating layer 52 may be applied in particular to the areas of electrically conductive layer 44 which have been left in method step b). For example, for the case that electrically conductive layer 44 is an oxidizable layer, electrically insulating layer 52 may be created in particular by a thermal oxidation process. In particular for the case that silicon is used as the electrically conductive material, electrically insulating cover layer 52 may be provided, for example, by an in particular thermal oxidation operation for creating silicon dioxide. This type of growth of the oxide layer may take place in particular as a function of the size and structure of recesses 46 introduced in method step b) or of the introduced structure, for example the diameter and position of the circular openings. For example, via such an embodiment the oxidation process may be automatically terminated when no more oxidizable material is exposed or is at a sufficiently small distance from the oxidizing atmosphere, since for oxide layers >500 nm, the diffusion through the oxide layer greatly limits the oxidation rate. Thus, oxidation may take place only where oxidizable material is present at a sufficiently small distance, for example <3 μm, which allows a defined structure without using masks, for example.

In particular, an oxidation operation may be advantageous in this method step c), since not only does the oxide, for example the silicon dioxide, grow into the material to be oxidized, for example the silicon, but in addition a portion of the oxide layer also grows outwardly. For example, 45%, for example, of the resulting oxide layer, such as in particular the silicon dioxide layer, grows into the silicon, and 55% grows out of the silicon. If the shape and/or size of recesses 46 are/is selected to be approximately the diameter of the circular openings and their in particular hexagonally tightest arrangement, a closed silicon dioxide layer may result in area ii), in the core of which a fine net of in particular highly doped silicon is buried, and which may be used as a net-like heating structure 28.

The recesses 46 introduced in a previous method step may therefore be closed, and the individual protrusions 48 may be partially or completely transferred into the oxide, such as silicon dioxide in particular, depending on the configuration or thickness. A thick oxide layer which may have a thickness of 20 μm, for example, may thus be created. An oxide layer having such a thickness, for example, may be used for the entire base body 22 or for the entire particle sensor 10, and does not have to be reduced to isolated island areas. In addition, it is apparent to those skilled in the art that base body 22 may be created from electrically insulating layers 42, 52.

Figures 6A, 6B:
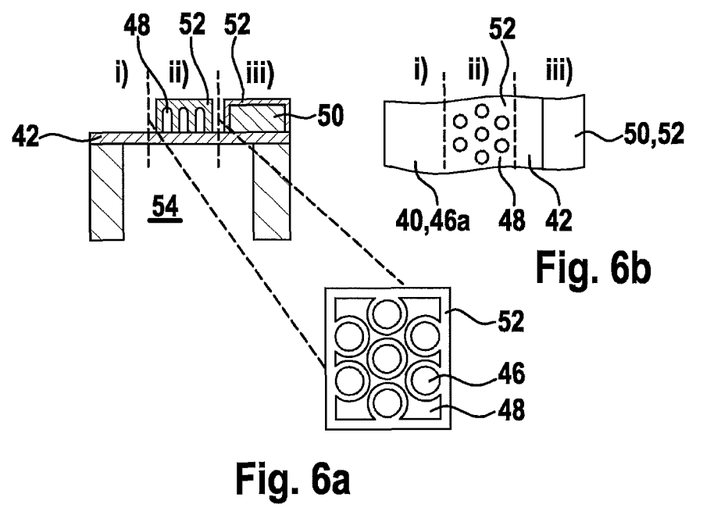
FIG. 6a shows a further method step for manufacturing a particle sensor, in a cross-sectional view.
FIG. 6b shows the method step from FIG. 6a in a top view.

In particular a net-like structure of the electrically conductive material may thus be created in this method step. This is shown in FIG. 6a, for example. In FIG. 6a the net-like electrically conductive structure, which may be used in particular as heating structure 28, is formed from in particular hexagonally arranged circular openings, made of silicon dioxide, for example, with electrically conductive material formed around same. The net-like conductor structure may be situated in base body 22. In addition, the conductor structure may include conducting tracks which, at least in part, have a thickness in a range of ≤500 nm or in the range of 100 nm. For example, this thickness may include the smallest conducting tracks which are situated, for example, between circular structures. As a result, they represent, at least locally or in part, a high electrical resistance, and may thus be used as an ohmic heater for heating structure 28.

FIG. 6 also shows a further optional method step. A portion 54 of base layer 40 may be removed in this method step, for example by deep etching on the rear side, whereby material is advantageously removed only up to electrically insulating layer 42, and electrically insulating layer 42 thus remains essentially unchanged and is exposed in this area.

Removing base layer 40 may have the advantage that the heat generated by heating structure 28 is not able to dissipate into this in particular thick layer, and heating may thus be localized to the desired area. As a result, this type of particle sensor 10 may heat in a particularly low-energy manner, and the requirements regarding the voltage or current used may be kept low.

In addition, an electrode system 20 which includes at least two electrode structures 14, 18 may be applied on electrically insulating layer 52 or on base body 22 in a further method step d). This method step is conventional, and may be implemented by deposition and structuring, for example. This method step d) is not shown in detail in the figures.

Figure 7:
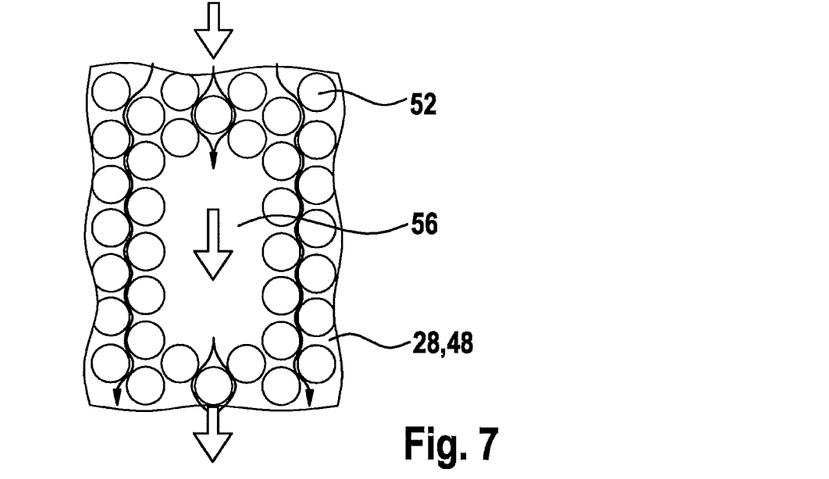
FIG. 7 shows another embodiment of a partial area of a particle sensor.

FIG. 7 shows another embodiment of a particle sensor 10. FIG. 7 shows that a homogenization area 56 of base body 22 for homogenizing the temperature of base body 22 generated by heating structure 28 may be provided, for example, in a central area of base body 22. Homogenization area 56 may be surrounded by net-like heating structure 28. In this embodiment, the electrical heat output may homogenize due to unstructured areas of a thermally and/or electrically conductive material, such as silicon in particular. This is because homogenization area 56 includes an area with low electrical resistance and high thermal conductivity. In particular the thermal resistance is low in this area, so that the heat may dissipate well or may be well distributed within heating structure 28 in base body 22. In addition, due to the low electrical resistance, little electrical heating takes place.

Figure 8:
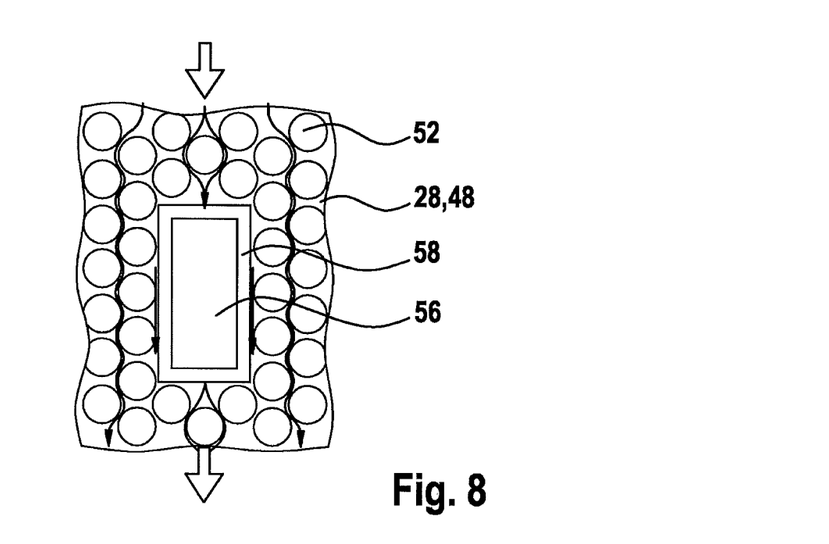
FIG. 8 shows another embodiment of a partial area of a particle sensor.

Homogenization area 56 may also be surrounded by an electrically insulating framing 58 which matches a depression having a closed contour and which is created in the same deep structuring process as for the net-like heating structure, as shown in FIG. 8. Electrically insulating framing 58, in particular made of silicon dioxide, may in turn be surrounded by heating structure 28. In this embodiment, a temperature homogenization in base body 22 may take place in particular due to high thermal conductivity of the silicon surfaces, but with only a small reduction in the electrical resistance. In this area, the heat may be concentrated in particular on the areas where it is actually needed.

In the embodiments according to FIGS. 7 and 8, for example, the thermally highly conductive silicon may thus result in a homogeneous temperature distribution on electrically insulating layer 42 or the silicon dioxide diaphragm, either by a suitable distribution of the electrical resistive heat output and thermal dissipation according to FIG. 7, or solely via thermal dissipation according to FIG. 8. This type of temperature homogenization may be advantageous, since, due to the better thermal insulation of a center area, higher temperatures may occur than at the diaphragm edges, which are better thermally coupled. Homogenization areas 56 shown in FIGS. 7 and 8 may have dimensions in a range of ≥10 μm to ≤20 μm, for example. A single homogenization area may be provided, for example in the middle of base body 22 or in the middle of heating structure 28, or a plurality of homogenization areas 56 may be provided which may be suitably arranged in order to homogenize or uniformly distribute the temperature in base body 22.

What is claimed is:

1. A particle sensor for detecting electrically conductive particles, comprising:
    a first electrode structure with at least one electrode; and
    a second electrode structure with at least one electrode;
    wherein the first electrode structure and the second electrode structure are situated on a same side of an electrically insulating base body, an electric potential difference being generatable between an electrode of the first electrode structure and an electrode of the second electrode structure, and
    wherein the base body includes a heating structure to heat the first electrode structure and the second electrode structure, the heating structure being at least partially enclosed by the base body,
    wherein the electrodes are not electrode nuclei since they function as electrodes without being exposed to the exhaust gas,
    wherein the first electrode structure and the second electrode structure form a system made up of interdigital electrodes which mesh together in a comb-like manner,
    wherein a homogenization area for homogenizing a temperature of the base body is provided which is surrounded by a net-like heating structure, the homogenization area being made of at least one of electrically and thermally conductive material, and
    wherein one of the following is satisfied:
        (i) the homogenization area includes a planar area in which a temperature plateau having maximum temperatures of up to +200° C. above the burnoff temperature, and wherein the homogenization area includes a planar extension and a settable electrically conductive material portion and/or a settable thermally conductive material portion, or
        (ii) the homogenization area is surrounded by an electrically insulating framing, which matches a depression having a closed contour, and which is enclosed by the net-like heating structure.

2. The particle sensor as recited in claim 1, wherein at least one of (i) the base body is made of silicon dioxide, and (ii) the heating structure is made of silicon.

3. The particle sensor as recited in claim 1, wherein the heating structure is completely enclosed by the base body.

4. The particle sensor as recited in claim 1, wherein the heating structure has a net-like conductor structure situated in the base body.

5. The particle sensor as recited in claim 4, wherein the net-like conductor structure includes conducting tracks which have, at least in part, a width in a range of ≤500 nm.

6. The particle sensor as recited in claim 1, wherein a homogenization area for homogenizing a temperature of the base body is provided which is surrounded by the heating structure, the homogenization area being made of at least one of electrically and thermally conductive material.

7. The particle sensor as recited in claim 6, wherein the homogenization area is surrounded by an electrically insulating framing which is enclosed by the heating structure.

8. The particle sensor as recited in claim 1, wherein the base body and the heating structure are situated in a first layer and the electrode structures are situated in a second layer, the second layer being situated on the first layer.

9. The particle sensor as recited in claim 1, wherein the base body includes silicon dioxide and the heating structure includes silicon.

10. The particle sensor as recited in claim 1, wherein the base body includes silicon nitride, aluminum oxide, and/or titanium oxide.

11. The particle sensor as recited in claim 1, wherein the heating structure includes metals having a melting point of >1000° C.

12. The particle sensor as recited in claim 1, wherein the heating structure includes titanium.

13. The particle sensor as recited in claim 1, wherein the electrode structures include platinum, tungsten, and/or silicon carbide.

14. The particle sensor as recited in claim 10, wherein the heating structure includes metals having a melting point of >1000° C.

15. The particle sensor as recited in claim 10, wherein the heating structure includes titanium.

16. The particle sensor as recited in claim 14, wherein the electrode structures include platinum, tungsten, and/or silicon carbide.

17. The particle sensor as recited in claim 1, wherein the net-like heating structure is formed by a net-like conductor structure, situated in the base body, and wherein the net-like conductor structure includes conducting tracks having a thickness in a range of ≤500 nm or in the range of 100 nm.

18. The particle sensor as recited in claim 1, wherein (i) is satisfied, so that the homogenization area includes the planar area in which the temperature plateau having maximum temperatures of up to +200° C. above the burnoff temperature, and wherein the homogenization area includes the planar extension and the settable electrically conductive material portion and/or the settable thermally conductive material portion.

19. The particle sensor as recited in claim 1, wherein (ii) is satisfied, so that the homogenization area is surrounded by the electrically insulating framing, which matches the depression having the closed contour, and which is enclosed by the net-like heating structure.

20. The particle sensor as recited in claim 19, wherein the net-like heating structure is formed by a net-like conductor structure, situated in the base body, and wherein the net-like conductor structure includes conducting tracks having a thickness in a range of ≤500 nm or in the range of 100 nm.

* * * * *